(12) United States Patent
Vetter et al.

(10) Patent No.: US 10,357,649 B2
(45) Date of Patent: Jul. 23, 2019

(54) NEURAL INTERFACE SYSTEM

(71) Applicant: Medtronic Bakken Research Center B.V., Maastricht (NL)

(72) Inventors: Rio J. Vetter, Ypsilanti, MI (US);
Daryl R. Kipke, Dexter, MI (US);
David Pellinen, Ann Arbor, MI (US);
David J. Anderson, Ann Arbor, MI (US); Jamille Farraye Hetke, Brooklyn, MI (US)

(73) Assignee: Medtronic Bakken Research Center B.V., Maastricht (NL)

( * ) Notice: Subject to any disclaimer, the term of this patent is extended or adjusted under 35 U.S.C. 154(b) by 32 days.

(21) Appl. No.: 15/433,701

(22) Filed: Feb. 15, 2017

(65) Prior Publication Data

US 2017/0224981 A1 Aug. 10, 2017

Related U.S. Application Data

(62) Division of application No. 14/245,250, filed on Apr. 4, 2014, now Pat. No. 9,604,051, which is a division
(Continued)

(51) Int. Cl.
*A61N 1/05* (2006.01)
*B29C 45/14* (2006.01)
(Continued)

(52) U.S. Cl.
CPC ......... *A61N 1/0534* (2013.01); *A61N 1/0539* (2013.01); *B29C 45/14639* (2013.01);
(Continued)

(58) Field of Classification Search
CPC ............ A61N 1/3605; A61N 1/36082; A61N 1/36021; A61N 1/36014; A61N 1/0551; A61N 1/0553
(Continued)

(56) References Cited

U.S. PATENT DOCUMENTS 3,847,687 A 11/1974 Davidsohn et al.
3,921,916 A 11/1975 Bassous
(Continued)

FOREIGN PATENT DOCUMENTS

WO 2001012115 A1 2/2001
WO 2001032551 A1 5/2001
(Continued)

OTHER PUBLICATIONS

Lin et al., "Silicon Processed Microneedles," IEEE J. Micro. Electro. Mech. Sys. vol. 8, No. 1 (1999) 78-84 (7 pages).
(Continued)

*Primary Examiner* — Catherine M Voorhees
*Assistant Examiner* — Roland Dinga
(74) *Attorney, Agent, or Firm* — Shumaker & Sieffert, P.A.

(57) ABSTRACT

The neural interface system of the preferred embodiments includes an electrode array having a plurality of electrode sites and a carrier that supports the electrode array. The electrode array is coupled to the carrier such that the electrode sites are arranged both circumferentially around the carrier and axially along the carrier. A group of the electrode sites may be simultaneously activated to create an activation pattern. The system of the preferred embodiment is preferably designed for deep brain stimulation, and, more specifically, for deep brain stimulation with fine electrode site positioning, selectivity, tunability, and precise activation patterning. The system of the preferred embodiments, however, may be alternatively used in any suitable environment (such as the spinal cord, peripheral nerve, muscle, or any other suitable anatomical location) and for any suitable reason.

5 Claims, 5 Drawing Sheets

Related U.S. Application Data of application No. 11/932,903, filed on Oct. 31, 2007, now Pat. No. 8,731,673.

(60) Provisional application No. 60/891,641, filed on Feb. 26, 2007.

(51) Int. Cl.
*A61B 5/04* (2006.01)
*A61N 1/36* (2006.01)
*B29K 83/00* (2006.01)
*B29L 31/00* (2006.01)

(52) U.S. Cl.
CPC ........ *A61B 5/04001* (2013.01); *A61N 1/36082* (2013.01); *B29K 2083/00* (2013.01); *B29L 2031/753* (2013.01)

(58) Field of Classification Search
USPC .............................................. 607/45, 46, 117
See application file for complete search history.

(56) References Cited

U.S. PATENT DOCUMENTS

| | | | |
|---|---|---|---|
| 4,053,977 A | 10/1977 | Simon et al. | |
| 4,141,365 A | 2/1979 | Fishcell et al. | |
| 4,166,469 A | 9/1979 | Littleford | |
| 4,306,562 A | 12/1981 | Osborne | |
| 4,455,192 A | 6/1984 | Tamai | |
| 4,461,304 A | 7/1984 | Kuperstein | |
| 4,465,482 A | 8/1984 | Tittel | |
| 4,762,135 A * | 8/1988 | van der Puije | A61N 1/0541 607/116 |
| 4,886,065 A | 12/1989 | Collins | |
| 4,904,237 A | 2/1990 | Janese | |
| 5,000,194 A * | 3/1991 | van den Honert | A61F 11/04 607/137 |
| 5,108,819 A | 4/1992 | Heller et al. | |
| 5,180,376 A | 1/1993 | Fischell | |
| 5,207,709 A | 5/1993 | Picha | |
| 5,215,088 A | 6/1993 | Normann et al. | |
| 5,308,442 A | 5/1994 | Taub et al. | |
| 5,322,064 A | 6/1994 | Lundquist | |
| 5,385,635 A | 1/1995 | O'Neill | |
| 5,390,671 A | 2/1995 | Lord | |
| 5,408,575 A | 4/1995 | Morris | |
| 5,409,469 A | 4/1995 | Schaerf | |
| 5,496,360 A | 3/1996 | Hoffmann et al. | |
| 5,515,848 A | 5/1996 | Corbett, III et al. | |
| 5,524,338 A | 6/1996 | Martyniuk et al. | |
| 5,573,520 A | 11/1996 | Schwartz et al. | |
| 5,585,827 A | 12/1996 | Murakami | |
| 5,588,597 A | 12/1996 | Reinecke et al. | |
| 5,720,099 A | 2/1998 | Parker et al. | |
| 5,744,958 A | 4/1998 | Werne | |
| 5,800,535 A * | 9/1998 | Howard, III | A61F 11/00 623/10 |
| 5,843,150 A | 12/1998 | Dreessen et al. | |
| 5,927,277 A | 7/1999 | Baudino et al. | |
| 5,938,694 A | 8/1999 | Jaraczewski et al. | |
| 5,975,085 A | 11/1999 | Rise | |
| 5,989,445 A | 11/1999 | Wise et al. | |
| 5,992,769 A | 11/1999 | Wise et al. | |
| 5,999,859 A * | 12/1999 | Jolly | A61N 1/0541 607/137 |
| 6,006,124 A | 12/1999 | Fischell et al. | |
| 6,016,449 A | 1/2000 | Fischell et al. | |
| 6,044,304 A | 3/2000 | Baudino | |
| 6,132,456 A | 10/2000 | Sommer et al. | |
| 6,181,569 B1 | 1/2001 | Chakravorty | |
| 6,205,361 B1 | 3/2001 | Kuzma et al. | |
| 6,228,111 B1 | 5/2001 | Tormala et al. | |
| 6,324,433 B1 | 11/2001 | Errio | |
| 6,325,797 B1 | 12/2001 | Stewart et al. | |
| 6,374,313 B1 | 4/2002 | Berrang et al. | |
| 6,430,443 B1 | 8/2002 | Karell | |
| 6,600,231 B2 | 7/2003 | Tominaga | |
| 6,618,623 B1 | 9/2003 | Pless et al. | |
| 6,829,498 B2 | 12/2004 | Kipke et al. | |
| 6,834,200 B2 | 12/2004 | Moxon et al. | |
| 6,878,643 B2 | 4/2005 | Krulevitch et al. | |
| 7,004,948 B1 | 2/2006 | Pianca et al. | |
| 7,006,859 B1 | 2/2006 | Osorio et al. | |
| 7,010,356 B2 * | 3/2006 | Jog | A61N 1/0551 600/373 |
| 7,011,680 B2 | 3/2006 | Alt | |
| 7,089,059 B1 | 8/2006 | Pless | |
| 7,181,288 B1 | 2/2007 | Rezai et al. | |
| 7,343,205 B1 | 3/2008 | Pianca et al. | |
| 7,548,775 B2 | 6/2009 | Kipke et al. | |
| 7,871,707 B2 | 1/2011 | Laude et al. | |
| 7,914,842 B1 | 3/2011 | Greenberg et al. | |
| 7,941,202 B2 | 5/2011 | Hetke et al. | |
| 8,731,673 B2 | 5/2014 | Vetter et al. | |
| 9,604,051 B2 | 3/2017 | Vetter et al. | |
| 2001/0006677 A1 | 7/2001 | Mcginity et al. | |
| 2001/0049499 A1 | 12/2001 | Lui et al. | |
| 2002/0052610 A1 | 5/2002 | Skakoon et al. | |
| 2002/0183817 A1 | 12/2002 | Van Venrooij et al. | |
| 2002/0198446 A1 | 12/2002 | Hill et al. | |
| 2003/0093129 A1 | 5/2003 | Nicolelis et al. | |
| 2003/0100823 A1 | 5/2003 | Kipke | |
| 2003/0114906 A1 | 6/2003 | Booker et al. | |
| 2003/0187461 A1 | 10/2003 | Chin | |
| 2004/0006264 A1 | 1/2004 | Moharradi et al. | |
| 2004/0102828 A1 | 5/2004 | Lowry et al. | |
| 2004/0106169 A1 | 6/2004 | Evans | |
| 2004/0199235 A1 | 10/2004 | Younis | |
| 2005/0004627 A1 | 1/2005 | Gibson et al. | |
| 2005/0004638 A1 * | 1/2005 | Cross, Jr. | A61N 1/0553 607/117 |
| 2005/0021116 A1 | 1/2005 | He et al. | |
| 2005/0021117 A1 | 1/2005 | He et al. | |
| 2005/0137647 A1 | 6/2005 | Wallace et al. | |
| 2005/0222647 A1 | 10/2005 | Wahlstrand et al. | |
| 2006/0122677 A1 | 6/2006 | Vardiman | |
| 2006/0173263 A1 | 8/2006 | He et al. | |
| 2006/0210610 A1 | 9/2006 | Davidson et al. | |
| 2006/0247749 A1 | 11/2006 | Colvin | |
| 2006/0258951 A1 * | 11/2006 | Bleich | A61B 17/1626 600/546 |
| 2006/0276866 A1 | 12/2006 | McCreery | |
| 2006/0282014 A1 | 12/2006 | Kipke et al. | |
| 2007/0073130 A1 | 3/2007 | Finch et al. | |
| 2007/0087036 A1 | 4/2007 | Durschlag et al. | |
| 2007/0122455 A1 | 5/2007 | Myers et al. | |
| 2007/0123765 A1 | 5/2007 | Hetke et al. | |
| 2007/0135885 A1 | 6/2007 | Risi | |
| 2008/0132970 A1 | 6/2008 | Barolat | |
| 2008/0255439 A1 | 10/2008 | Tang et al. | |
| 2008/0262584 A1 | 10/2008 | Bottomley et al. | |
| 2009/0099555 A1 | 4/2009 | Viohl et al. | |
| 2009/0102068 A1 | 4/2009 | Pellinen et al. | |
| 2009/0118806 A1 | 5/2009 | Vetter et al. | |
| 2009/0132042 A1 | 5/2009 | Hetke et al. | |
| 2009/0149934 A1 | 6/2009 | Ameri et al. | |
| 2009/0149937 A1 | 6/2009 | Ameri et al. | |
| 2009/0171421 A1 | 7/2009 | Atalar et al. | |
| 2009/0187196 A1 | 7/2009 | Vetter | |
| 2009/0234426 A1 | 9/2009 | Pellinen et al. | |
| 2009/0240314 A1 | 9/2009 | Kong et al. | |
| 2009/0248118 A1 | 10/2009 | Bradley et al. | |
| 2009/0253977 A1 | 10/2009 | Kipke et al. | |
| 2009/0299167 A1 | 12/2009 | Seymour | |
| 2009/0312770 A1 | 12/2009 | Kozai et al. | |
| 2010/0030298 A1 | 2/2010 | Martens et al. | |
| 2010/0145216 A1 | 6/2010 | He et al. | |
| 2010/0145422 A1 | 6/2010 | Seymour et al. | |

(56) References Cited

U.S. PATENT DOCUMENTS

| | | |
|---|---|---|
| 2011/0093052 A1 | 4/2011 | Anderson et al. |
| 2011/0154655 A1 | 6/2011 | Hetke |

FOREIGN PATENT DOCUMENTS

| | | |
|---|---|---|
| WO | 2001097906 A1 | 12/2001 |
| WO | 2002041666 A1 | 5/2002 |
| WO | 2002096482 A2 | 12/2002 |
| WO | 2005039696 A1 | 5/2005 |
| WO | 2006138358 A2 | 12/2006 |
| WO | 2007042999 A2 | 4/2007 |
| WO | 2007089738 A2 | 8/2007 |
| WO | 2008011721 A1 | 1/2008 |
| WO | 2008038208 A2 | 4/2008 |
| WO | 2008072125 A1 | 6/2008 |
| WO | 2008109298 A1 | 9/2008 |
| WO | 2009052421 A1 | 4/2009 |
| WO | 2009052423 A1 | 4/2009 |
| WO | 2009052425 A1 | 4/2009 |
| WO | 2010057095 A2 | 5/2010 |
| WO | 2011010257 A1 | 1/2011 |
| WO | 2011046665 A1 | 4/2011 |

OTHER PUBLICATIONS

Seymour, John et al., "Neural probe design for reduced tissue encapsulation in CNS," 28 (2007) 3594-3607, Apr. 5, 2007.
Seymour, John et al., "The insulation performance of reactive parylene films in implantable electronic device," Biomaterials, 30 (2009), 6158-6167, Aug. 22, 2009.
Kaplan et al., "A Novel Fabrication Method of Capillary Tubers on Quartz for Chemical Analysis Applications," IEEE Proceedings, Micro Electro Mechanical Systems, Jan. 25-28, 1994.
Lin et al., "Silicon Processed Microneedles," The 7th International Conference on Solid State Sensors and Acutators; Jun. 7-10, 1993.
International Search Report and Written Opinion from International Application No. PCT/US08/55025, dated Oct. 27, 2008, 5 pp.
International Preliminary Report on Patentability from International Application No. PCT/US08/55025, dated Aug. 26, 2009, 6 pp.
International Search Report from International Application No. PCT/IB06/53700, dated Nov. 21, 2008, 4 pp.
International Preliminary Report on Patentability from International Application No. PCT/IB06/53700, dated Mar. 10, 2009, 5 pp.
International Search Report and Written Opinion from International Application No. PCT/IB10/53250, dated Oct. 4, 2010, 10 pp.
International Preliminary Report on Patentability from International Application No. PCT/IB10/53250, dated Jan. 24, 2012, 7 pp.
International Search Report from International Application No. PCT/US2004/035030, dated Feb. 21, 2006, 5 pp.
International Preliminary Report on Patentability from International Application No. PCT/US2004/035030, dated Apr. 24, 2006, 6 pp.
International Search Report from International Application No. PCT/US06/23139, dated Aug. 2, 2007, 4 pp.
International Preliminary Report on Patentability from International Application No. PCT/US06/23139, dated Dec. 17, 2007, 5 pp.
International Search Report from International Application No. PCT/US07/02465, dated Feb. 13, 2008, 4 pp.
International Preliminary Report on Patentability from International Application No. PCT/US07/02465, dated Jul. 29, 2008, 5 pp.
International Search Report from International Application No. PCT/US08/80366, dated Dec. 10, 2008, 5 pp.
International Preliminary Report on Patentability from International Application No. PCT/US08/80366, dated Apr. 20, 2010, 6 pp.
International Search Report from International Application No. PCT/US2009/064591, dated Jul. 21, 2010, 8 pp.
International Preliminary Report on Patentability from International Application No. PCT/US2009/064591, dated May 17, 2011, 6 pp.
International Search Report from International Application No. PCT/US2010/044167, dated Sep. 27, 2010, 8 pp.
International Preliminary Report on Patentability from International Application No. PCT/US2010/044167, dated Apr. 17, 2012, 7 pp.
International Search Report from International Application No. PCT/US2008/080362, dated Dec. 22, 2008, 7 pp.
International Preliminary Report on Patentability from International Application No. PCT/US2008/080362, dated Apr. 20, 2010, 8 pp.
Prosecution History from U.S. Appl. No. 11/932,903, dated from Sep. 28, 2010 through Jan. 13, 2014, 64 pp.
Prosecution History from U.S. Appl. No. 14/245,250, dated from Apr. 4, 2016 through Nov. 15, 2016, 31 pp.

* cited by examiner

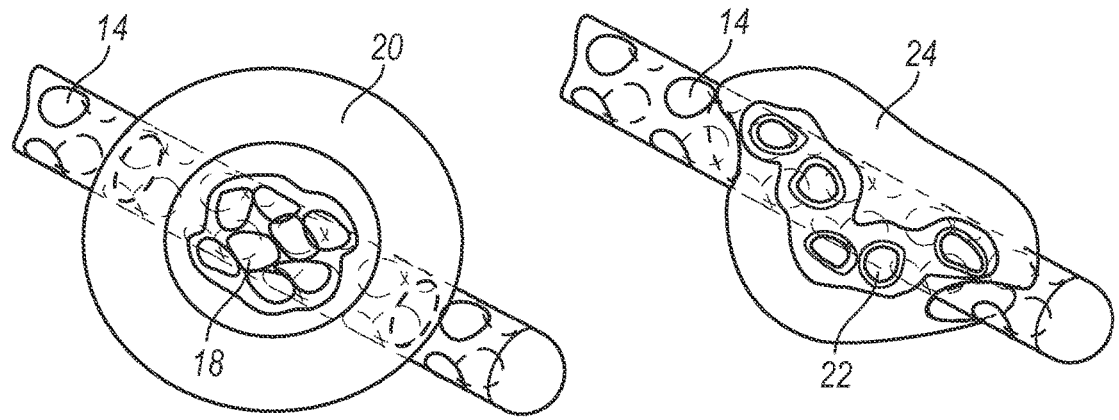
FIG. 3A
FIG. 3B
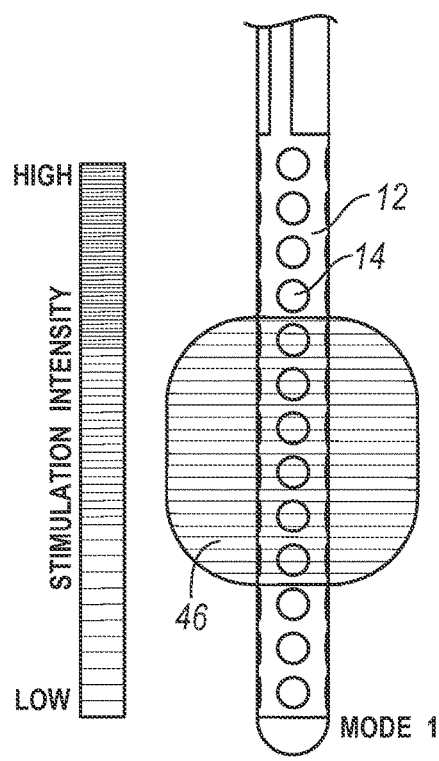
FIG. 4A
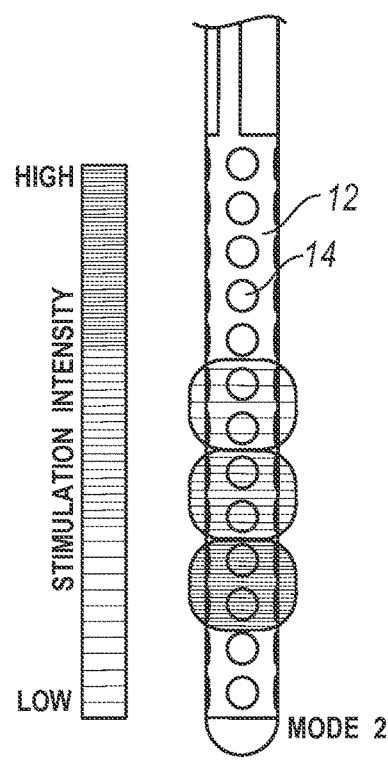
FIG. 4B

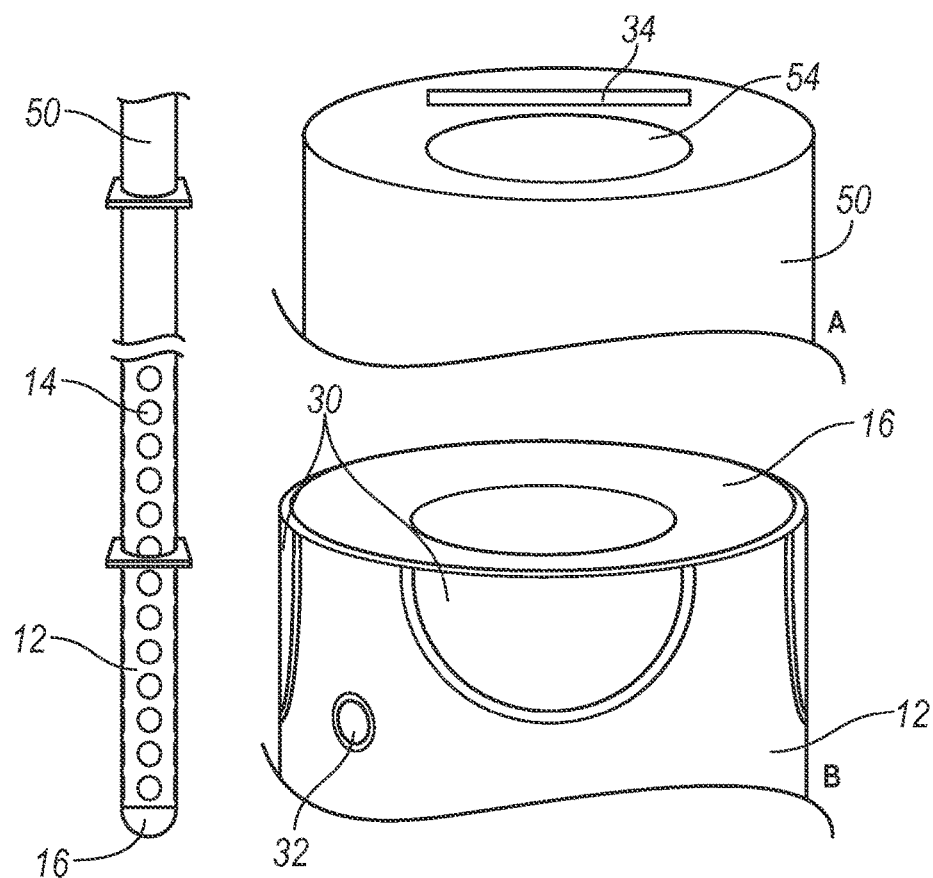
FIG. 7
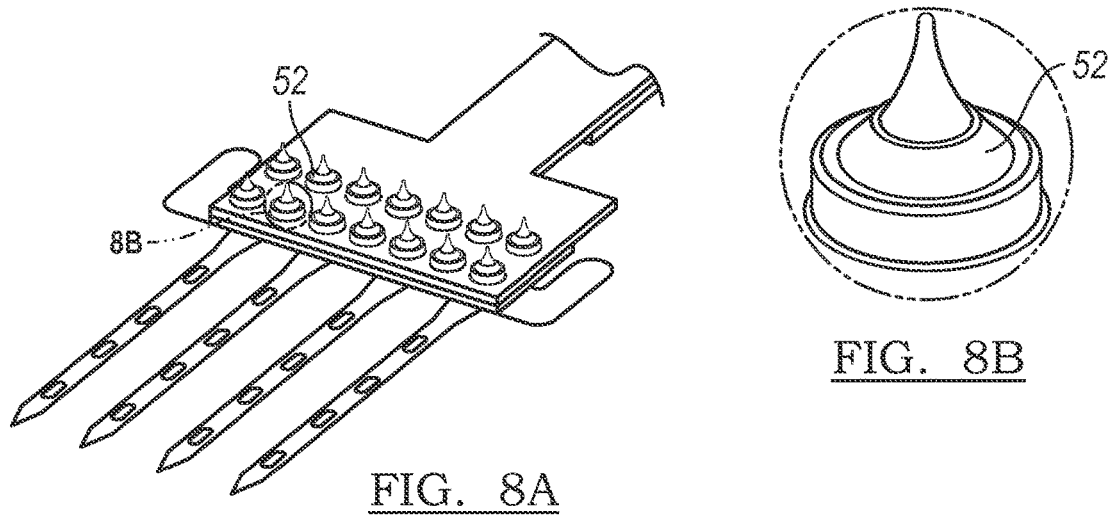
FIG. 8A
FIG. 8B

NEURAL INTERFACE SYSTEM

CROSS-REFERENCE TO RELATED APPLICATIONS

This application is a divisional of U.S. application Ser. No. 14/245,250, filed Apr. 4, 2014, which is a divisional of U.S. application Ser. No. 11/932,903, filed Oct. 31, 2007, which claims the benefit of U.S. Provisional Application No. 60/891,641, filed Feb. 26, 2007, the entirety of which are incorporated herein by reference.

TECHNICAL FIELD

This invention relates generally to the neural interface field, and more specifically to an improved neural interface system having an electrode array with a series of electrode sites.

BACKGROUND

Chronic Deep Brain Stimulation (DBS) devices—'brain pacemakers'—have emerged in the last decade as a revolutionary new approach to the treatment of neurological and psychiatric disorders. Conventional DBS therapy involves controllable electrical stimulation through a lead having four relatively large electrodes that are implanted in the targeted region of the brain. While conventional DBS therapy is generally safe and effective for reducing cardinal symptoms of the approved diseases, it often has significant behavioral and cognitive side effects and limits on performance. Additionally, the therapeutic effect is highly a function of electrode position with respect to the targeted volume of tissue, and more specifically, a function of which neuronal structures are influenced by the charge being delivered. With conventional electrodes, there are limitations as to how the charge is delivered and stimulation fields are limited as all of the electrode sites involved with stimulation are positioned along a single axis. Thus, there is a need for an improved neural interface system to provide fine electrode positioning, selectivity, precise stimulation patterning, and precise lead location. This invention provides such an improved and useful neural interface system.

BRIEF DESCRIPTION OF THE FIGURES

FIGS. 3A and 3B are schematic drawings of a first group of electrode sites and a first activation pattern and a second group of electrode sites and a second activation pattern respectively.

FIGS. 4A and 4B are schematic drawings of activation patterns and activation intensities.

FIG. 7 is a cross-sectional drawing of the silicone element, the carrier, and the electrode array.

FIGS. 8A and 8B are schematic drawings of ball bonds.

DESCRIPTION OF THE PREFERRED EMBODIMENTS

The following description of preferred embodiments of the invention is not intended to limit the invention to these embodiments, but rather to enable any person skilled in the art to make and use this invention.

Figure 1A:
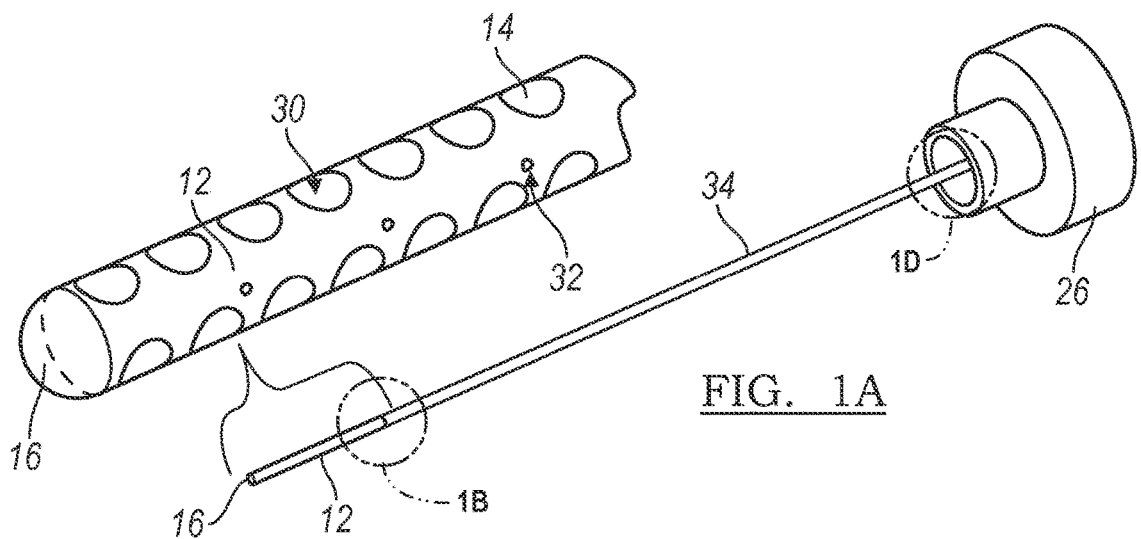
FIGS. 1A, 1B, 1C, and 1D are schematic drawings of the neural interface system, in accordance with one or more techniques of this disclosure.

As shown in FIG. 1A, the neural interface system 10 of the preferred embodiments includes an electrode array 12 having a plurality of electrode sites 14. The electrode sites may be individually activated or simultaneously activated as a group to create an activation pattern. In alternative preferred embodiments, the neural interface may further include a carrier 16 that supports the electrode array. The electrode array 12 is coupled to the carrier 16 such that the plurality of electrode sites 14 are arranged both circumferentially around the carrier 16 and axially along the carrier 16. The system 10 of the preferred embodiment is preferably designed for deep brain stimulation, and, more specifically, for deep brain stimulation with fine electrode site positioning, selectivity, tunability, and precise activation patterning. The system 10 of the preferred embodiments, however, may be alternatively used in any suitable environment (such as the spinal cord, peripheral nerve, muscle, or any other suitable anatomical location) and for any suitable reason.

1. The Electrode Array

The electrode array 12 of the preferred embodiments functions to interface with the tissue, or any other suitable substance, that it has been implanted in or coupled to. The electrode array 12 includes a plurality of electrode sites 14 such that a group of the electrode sites 14 may be simultaneously activated to create an activation pattern. The electrode array 12 provides the capability of incorporating feedback control through neural recordings for eventual on-demand stimulation. The electrode array 12 may further include fluidic channels providing the capability to deliver therapeutic drugs, drugs to inhibit biologic response to the implant, or any other suitable fluid.

The electrode array 12 is preferably one of several variations. In a first variation, the electrode array 12 is a planar array. In this variation, the electrode array 12 would be particularly useful for stimulation of surface tissue such as surface stimulation of the brain or spinal cord. In a second variation, the electrode array 12 has a three dimensional geometry. The geometry preferably has a circular or semicircular cross section, but may alternatively be any suitable geometry with any suitable cross section such as a v-shaped cross section. The planar electrode array 12 is preferably pre-formed into the three dimensional geometry. This is preferably completed by positioning the planar electrode array 12 in a mold and then placing the mold and electrode array 12 in a furnace to be tempered, but may alternatively be completed by any suitable process that alters the physical shape of the planar substrate. The electrode array 12 in this variation, may be wrapped directly around the tissue to be stimulated such as a peripheral nerve or spinal cord. The electrode array 12 of the second variation may be coupled to the carrier 16. The electrode array 12 is preferably coupled to the carrier 16 such that the plurality of electrode sites 14 are arranged both circumferentially around the carrier 16 and axially along the carrier 16. Although the electrode array 12 is preferably one of these variations, the electrode array 12 may be in any suitable configuration to interface with the tissue, or any other suitable substance, that it has been implanted in or coupled to.

The neural interface system 10 may include a single electrode array 12 with a plurality of electrode sites 14 or may alternatively include a series of electrode arrays 12, each with a plurality of electrode sites 14. The neural interface system 10 may further include a guiding element that positions the series of electrode arrays 12 in a three dimensional arrangement, or the electrode arrays 12 may alternatively be arranged in a three dimensional manner without an additional guiding element. The neural interface system 10 may include one guiding element for every electrode array 12, such that the ratio of guiding elements to electrode arrays 12 is 1:1. Alternatively, the neural interface system 10 may include one guiding element for every two or more electrode arrays 12, such that the ratio of guiding elements to first electrode arrays 12 is less than 1:1. Additionally, the guiding elements may be coupled to a chamber 26, as shown in FIG. 2, or any other suitable element of the neural interface system 10 and may include a sharpened end adapted to penetrate the tissue and aid in the insertion of the electrical subsystems and/or guiding elements into the tissue.

Figure 2:
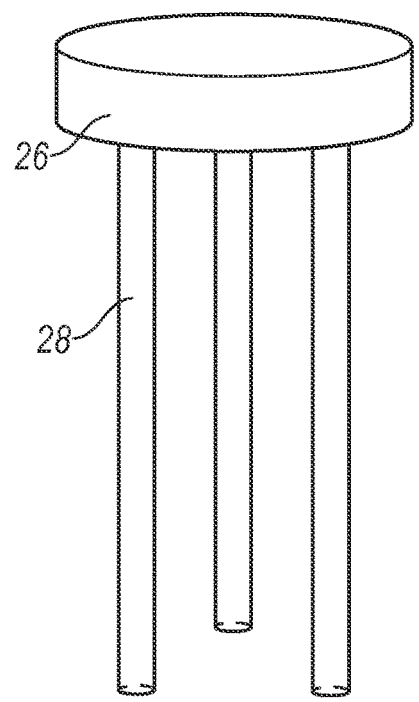
FIG. 2 is a schematic drawing of the series of electrode arrays and guiding elements.

As shown in FIG. 2, the guiding element is preferably a rigid guiding element 28. The guiding element may be a stylet, a guide tube, a connector 34, or any other suitable guiding element. In this variation, the rigid guiding element 28 guides the electrode arrays 12 into a three-dimensional arrangement along predetermined trajectories. The rigid guiding elements 28 preferably implant the electrode arrays into a specific location and a specific three-dimensional spatial distance from one another determined by the location of the guiding elements 28. For example, as shown in FIG. 2, the guiding elements 28 are positioned at a specific location and a specific three-dimensional spatial distance from one another prior to implantation. Upon insertion of the rigid guiding elements 28 and the series of electrode arrays 12 the guiding elements 28 will move the electrode arrays 12 along the predetermined trajectory into the corresponding specific location and three-dimensional spatial distance from one another as the guiding elements 28. The trajectories are preferably parallel, but may alternatively be at any suitable angle to one another to implant the series of electrode arrays 12 into a three-dimensional arrangement. The material of the rigid guiding element 28 is preferably a generally rigid material such as metal or plastic, but may alternatively be made from any suitable material.

2. The Plurality of Electrode Sites

The plurality of electrode sites 14 of the preferred embodiments functions to electrically communicate with the tissue, or any other suitable substance, that it has been implanted in or coupled to. The electrical communication is preferably a high-frequency, pulsed electric current; electrical stimulation in monopolar, bipolar, tripolar, and/or quadrapolar modes; a recording of electrical signals; data transmission; and/or any other suitable electrical communication.

The plurality of electrode sites 14 can be activated individually or in selectable groups of electrode sites. The simultaneous activation of a group of electrode sites 14 creates an activation pattern, generates an electric field in the tissue medium having a spatial distribution of current density, and influences the pattern of neural excitation. This will provide dynamic tunable electrical stimulation ranging from macroscale activation, as shown in FIG. 3A and 4A, to more selective directional activation patterning using smaller groups of sites along or around the carrier, as shown in FIG. 3B and 4B. Additionally, each of the electrode sites 14 may be activated with an independent activation intensity. As shown in FIGS. 4A and 4B each activation intensity may be individually distinct, or groups of electrode sites may each have the same activation intensity.

Figure 5A:
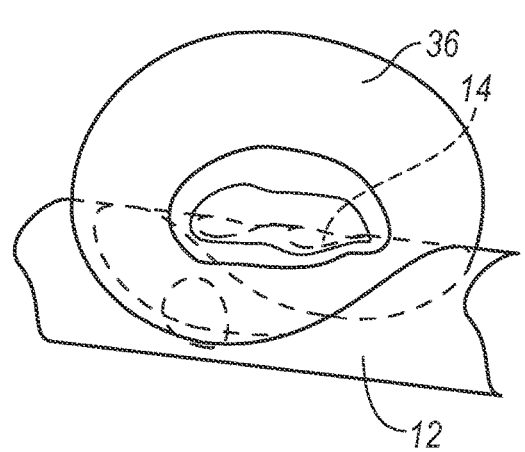
FIGS. 5A and 5B are schematic drawings of an activation pattern along the carrier and an activation around the carrier respectively.
Figure 5B:
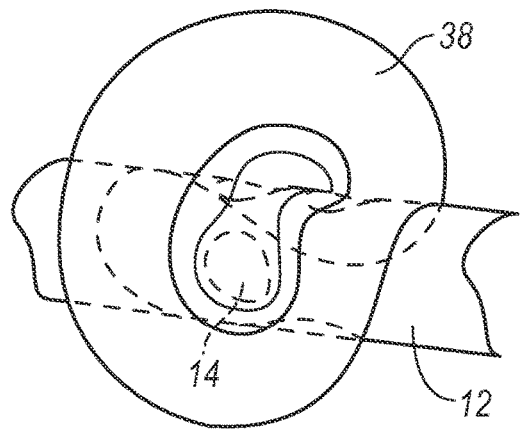
Figure 6:
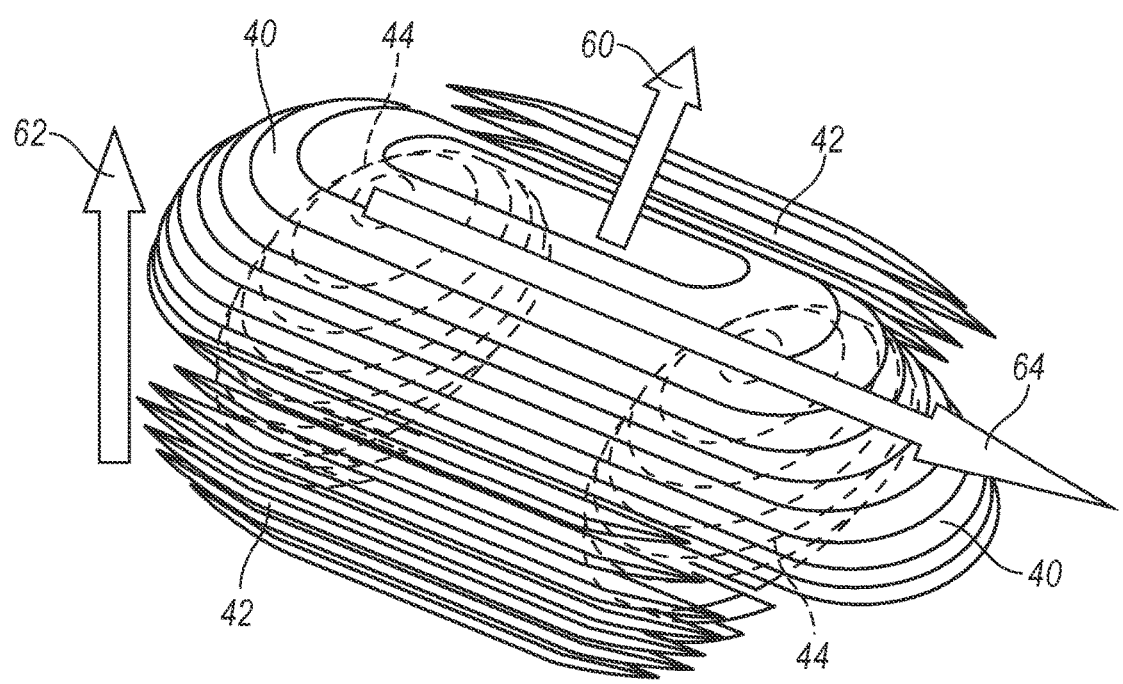
FIG. 6 is a schematic drawing of excitation volumes along three different dimensions of tissue.

As shown in FIGS. 5A and 5B, activation patterns from an electrode array 12 can be translated not only axially up and down a carrier 16 (FIG. 5A), but also side-to-side or circumferentially around the carrier 16 (FIG. 5B) thus allowing for slight corrections in the position of the electrode by electrical means. As shown in FIGS. 5A and 5B, the activation patterns 36 and 38 (shown as isopotential contours) are each created by the activation of two electrode sites 14. Noting that curvature and direction of curvature of isopotential surfaces indicate magnitude and direction of second spatial derivative, the preferred direction of excitation can be adjusted by the choice of sites activated in an array. An activation pattern generates excitation volumes that are specific for neural fibers or axons traveling in the three principle directions of the electrode array 12. As shown in FIG. 6, the excitation volumes 40, 42, and 44 are generated by an activation pattern, specifically the activation pattern shown in FIG. 5A. The first excitation volume 40 is for axon orientation perpendicular (as shown by arrow 60) to the electrode and above it, the second excitation volume 42 is for vertically traveling axons (as shown by arrow 62), and the third excitation volume 44 is for axons traveling parallel (as shown by arrow 64) to the electrode.

As shown in FIGS. 3A and 3B, a group of the electrode sites are simultaneously activated to create an activation pattern. As shown in FIG. 3A, activating a first group of electrode sites 18 creates a first activation pattern 20. The first group of electrode sites 18 includes each of the electrode sites around the circumference of the carrier 16 at a particular axial location. As shown in FIG. 3B, activating a second group of electrode sites 22 creates a second activation pattern 24. The second group of electrode sites 22 includes electrode sites at multiple axial locations and less than each of the electrode sites around the circumference of the carrier at a particular axial location.

The excitation of tissue surrounding an electrode site 14 is determined by electrochemical properties of the individual electrode site and by geometric properties of the entire electrode array and carrier assembly. For an electrode array 12 with several electrode sites 14 activated simultaneously, the activation pattern, and therefore the current flow surrounding the electrode, is complex resulting in an equally complex pattern of tissue excitation. At a basic level, the spreading resistance of an electrode site may determine the ability of the site to deliver charge to excitable tissue. When several electrode sites 14 on an electrode array 12 are activated simultaneously there is an interaction of the electrode sites and activation patterns. For example, the second activation pattern, as shown in FIG. 3B, may be modulated with the activation of a third distinct group of electrode sites 14. Furthermore, multiple groups of activated electrode sites can be overlapping or nonoverlapping.

In one specific variation of the electrode array 12, as shown in FIG. 1A, the electrode array 12 preferably includes sixty-four stimulation electrode sites 30 and thirty-two recording electrode sites 32 positioned circumferentially around and axially along the carrier 16. Each stimulation electrode site 30 has a surface area of preferably 0.196 mm$^2$ (diameter=500 μm), but may alternatively have any suitable surface area. Each recording electrode site 32 has a surface area of preferably 0.00196 mm$^2$ (diameter=50 μm), but may alternatively have any suitable surface area. The stimulation electrode sites 30 are preferably positioned such that four sites will be equally spaced around the circumference of the carrier 16 (center-to-center spacing is about equal to 750 μm). Sites will also be preferably spaced at 750 μm in the axial direction (center-to-center) and positioned at sixteen successive locations. Between each row of stimulation electrode sites 30, two recording electrode sites 32 will preferably be positioned on opposite sides of the carrier 16. The positions of each recording electrode site pair will preferably shift ninety degrees between successive depths. Alternatively, there may be any suitable number of stimulation electrode sites 30 and recording electrode sites 32, and the stimulation electrode sites 30 and recording electrode sites 32 may alternatively be positioned in any other suitable arrangement.

3. Fabrication of The Electrode Array and The Plurality of Electrode Sites

The electrode array 12 is preferably made from a thin-film polymer substrate (or any other suitable material) such that there is high density of electrode sites 14 at a first end of the array (the distal end) and bonding regions at a second end of the array (the proximal end). The proximal end is preferably thicker than the distal end of the electrode array 12 to accommodate the bonding regions or the integration of a second electrical subsystem. The polymer substrate is preferably parylene or some combination of parylene and inorganic dielectrics, but may alternatively be made out of any suitable material. The distal end of the array is preferably coupled to a carrier 16 to provide structural support. Additionally, the distal end will be in direct contact with the tissue and so will preferably be made from suitable materials for both biocompatibility and dielectrics.

In general, the fabrication techniques for the electrode array 12 are preferably similar to those used to create integrated circuits and therefore preferably utilize similar substrate, conductor and insulating materials. Fabrication of the electrode array 12 preferably starts on a wafer substrate and the electrode sites 14 and additional features are preferably added using a number of photolithographically patterned thin-film layers that are preferably defined by etching. The electrode arrays 12 produced in this manner are preferably reproducible, batch-processed devices that have features preferably defined to within less than +/−1 μm. In addition, many of the fabrication techniques are preferably compatible with the inclusion of an integrated flexible ribbon cable or connector 34 and a second electrical subsystem such as on-chip circuitry for signal conditioning and/or stimulus generation.

Polymer electrode arrays preferably include metal traces sandwiched between upper and lower layers of insulating polymer. One such polymer is parylene (parylene-C, Specialty Coating Systems, Indianapolis, Ind., USA). The polymer is vapor phase deposited onto an oxidized silicon wafer that acts as a carrier. A layer of photoresist is then spun on and patterned in preparation for metal lift-off. Layers of titanium and platinum are preferably next deposited and patterned using lift-off. The top layer of polymer is then vapor phase deposited. The wafers are then preferably patterned and dry-etched to form the final electrode shape and create openings to the underlying metal. These metal surfaces form the electrode sites and additional features such as conductive interconnects and bond pads. HF dissolution of the oxide release layer is used to remove the devices from the wafer. The devices are finally cleaned using multiple soaks and rinses in DI water. Presently, the process requires only two photolithographic masks resulting in rapid turnaround for easy design iteration.

The electrode sites 14 are preferably patterned directly onto the polymer substrate. The electrode sites 14 are preferably metal such as iridium, platinum, gold, but may alternatively be any other suitable material. Iridium oxide is preferably used for the electrode sites 14 due to its high charge capacity (3 mC/cm$^2$). The targeted charge injection limit for the activation pattern 46 as shown in FIG. 4A is preferably 500 nC/cm$^2$, while preferably maintaining a safe charge density of 30 μC/cm$^2$. The targeted composite impedance (electrode contact plus lead) is preferably 10 kΩ (stimulating contacts) and 100 kΩ (recording contacts). Impedance matching will preferably occur across all sites. Each site will preferably be electrically isolated with crosstalk preferably below 1%.

The electrode array 12 preferably further includes conductive interconnects disposed between layers of dielectrics that insulate the interconnects on top and bottom sides. Preferably a group of the conductive interconnects terminate with electrode sites 14 on the distal end and/or with bond pads for electrical connection to external instrumentation and/or hybrid chips on the proximal end. The conductive interconnects are preferably metal or polysilicon, but may alternatively be any other suitable material. Polyimide, parylene, inorganic dielectrics, or a composite stack of silicon dioxide and silicon nitride is preferably used for the dielectrics, however any other suitable materials may alternatively be used.

Figure 1B:
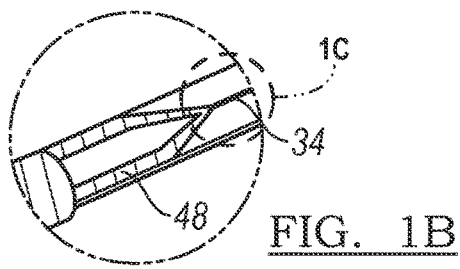
Figure 1C:
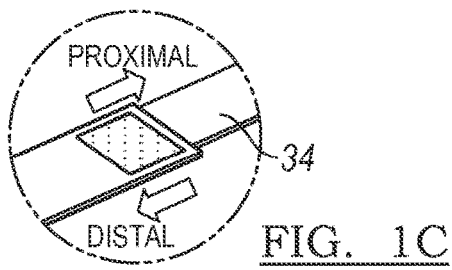
Figure 1D:
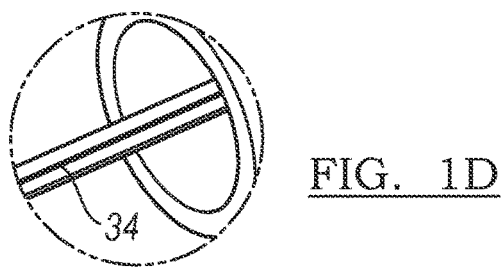

The conductive interconnects are preferably made as wide as possible to reduce the resistance. The conductive interconnects will vary in length as they terminate at different locations, and so in order to equalize the resistance across all leads, the line widths are preferably adjusted accordingly. These conductive interconnects, as well as the connections will be preferably buried in silicone and thus not be at risk to leakage, as shown in FIG. 1D. The electrode array 12 will function more efficiently if all the impedances of the conductive interconnects are equal as seen from the bonding area. This is preferably accomplished by increasing the width of the longer traces. Preferably, the width of each segment of each conductive interconnect is optimized using a "hill climbing" method. A layout program preferably generates polygons representing the several conductive interconnects.

4. The Carrier

Figure 9A:
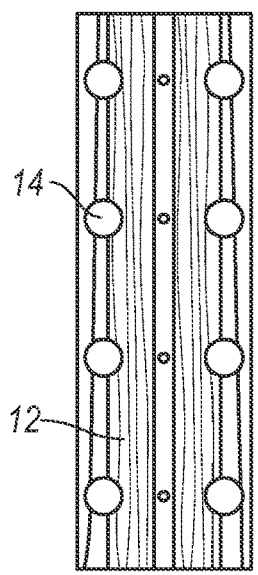
FIGS. 9A and 9B are schematic drawings of the electrode array, the plurality of electrode sites, and the carrier.
Figure 9B:
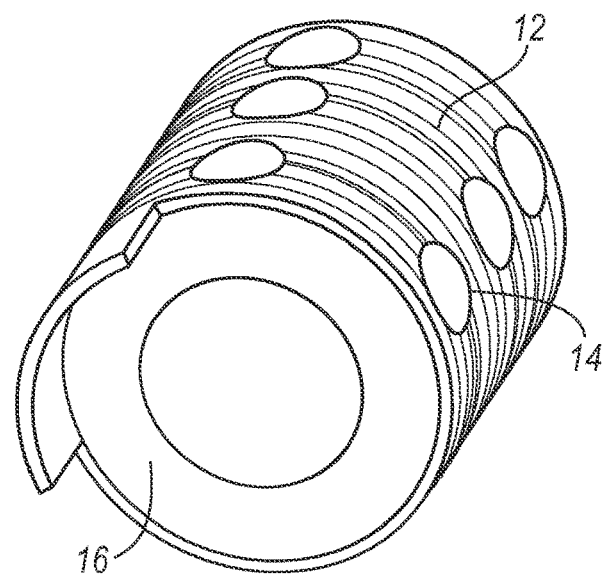

The carrier 16 of the preferred embodiments, as shown in FIGS. 9A and 9B, functions to support the electrode array 12. The carrier 16 may further function to shuttle the electrode array 12 into tissue or other substances. The shape of the carrier 16 is preferably tubular with about a 1-mm diameter, but may alternatively be any suitable shape of any suitable diameter for the desired functions. The carrier 16 may include a sharpened end adapted to penetrate the tissue and aid in the insertion of the carrier 16 and the electrode array 12 into the tissue. The carrier 16 may further extend the functionality of the system by providing fluidic channels through which therapeutic drugs, drugs to inhibit biologic response to the implant, or any other suitable fluid may be transmitted. This provides for the precise delivery of specific pharmaceutical compounds to localized regions of the body, such as the nervous system, and could facilitate, for example, intraoperative mapping procedures or long-term therapeutic implant devices. The fluidic channels may also provide a location through which a stiffener or stylet may be inserted to aid with implantation. Alternatively, the carrier 16 may further include a separate lumen through which the stiffener or stylet may be inserted.

The carrier 16 is preferably one of several variations. In a first variation, the carrier 16 is a polymeric carrier 16. The carrier 16 is preferably made of a polymer such as polyimide or silicone, but may be alternatively made from any other suitable material. The carrier 16 is preferably flexible, but may alternatively be rigid or semi rigid. In a second variation, the carrier 16 is a metal carrier. The carrier in this variation may be a solid metal tube or cylinder, or it may alternatively be perforated or not solid in any other suitable fashion. In a third variation, the carrier 16 is resorbable carrier 16, which is resorbed into tissue after a period of time, and upon resorption, the electrode array 12 will be left to float freely in the brain or other suitable tissue or material. The resorbable carrier 16 is preferably made of implantable medical fabric woven or knitted from a bioresorbable polymer. The bioresorbable polymer is preferably polyglycolide or polylactide, but may alternatively be made from any suitable bioresorbable material. Although the carrier 16 is preferably one of these three variations, the carrier 16 may be any suitable element to shuttle the electrode array 12 and the connector 34 into tissue or other substances and provide structural support.

5. The Second Electrical Subsystem and the Connector

Figure 10A:
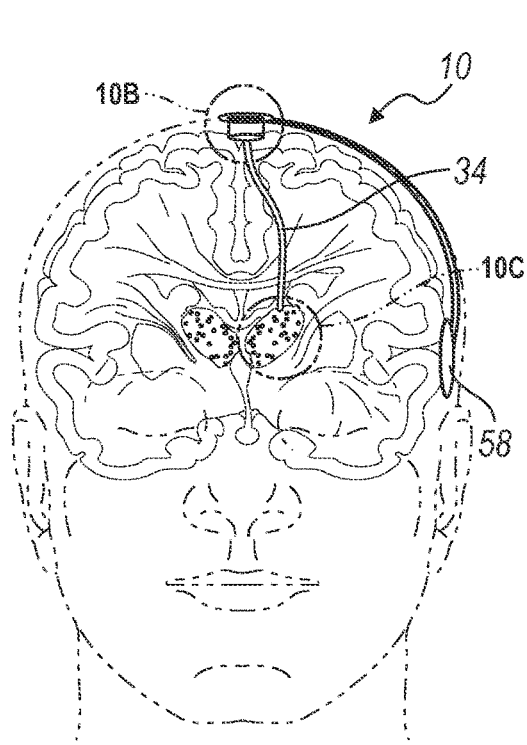
FIGS. 10A, 10B, and 10C are schematic drawings of the neural interface system implanted in a patient.
Figure 10B:
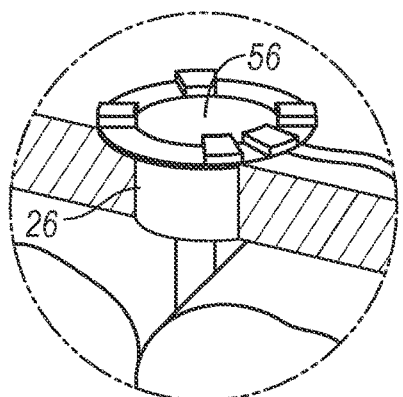
Figure 10C:
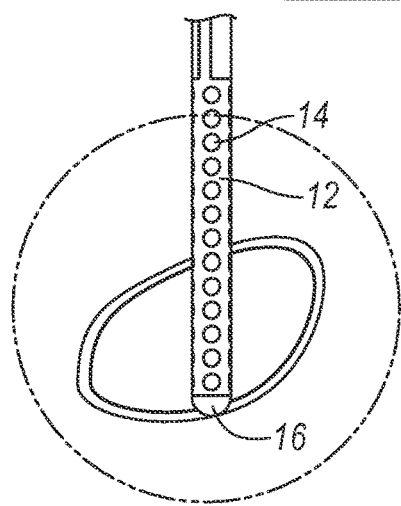

Additionally, the system 10 may further include a second electrical subsystem. The second electrical subsystem of the preferred embodiments functions to operate with the electrode array 12. The second electrical subsystem may include multiple different electrical subsystems or a series of the same subsystems. The second electrical subsystem may be integrated into the proximal end of the electrode array 12 or may be coupled to the electrode array 12 via a connector 34 as described below. The second electrical subsystem is preferably at least one of several variations of suitable electronic subsystems to operate with the electrode array 12 or any combination thereof. The second electrical subsystem may be a printed circuit board with or without on-board integrated circuits and/or on-chip circuitry for signal conditioning and/or stimulus generation, an Application Specific Integrated Circuit (ASIC), a multiplexer chip, a buffer amplifier, an electronics interface, an implantable pulse generator (produces a high-frequency, pulsed electric current), an implantable rechargeable battery, integrated electronics for either real-time signal processing of the input (recorded) or output (stimulation) signals, integrated electronics for control of the fluidic components, any other suitable electrical subsystem, or any combination thereof. In one specific variation, as shown in FIGS. 10A-10C, the neural interface system 10 includes an electrode array 12, an electronics interface 56 and implantable pulse generator located in a cranial burr-hole chamber, and an implantable rechargeable battery 58. Although the second electrical subsystem is preferably one of these several subsystems, the second electrical subsystem may be any suitable element or combination of elements to operate the electrode array 12.

Additionally, the system 10 may further include a connector 34. The connector 34 of the preferred embodiments functions to couple the electrode array 12 to the second electrical subsystem. The connector 34 is preferably one of several variations. As shown in FIGS. 1A-1D, the connector 34 is preferably a flexible ribbon cable. The ribbon cable is preferably polymer ribbon cable, but may alternatively be any other suitable ribbon cable. The connector 34 may alternatively be any suitable element to couple the electrode array 12 to the second electrical subsystem, such as wires, conductive interconnects, etc.

The ribbon cable may be encased in silicone or any other suitable material, as shown in FIGS. 1D and 7. In some situations, the electrical subsystem may have multiple ribbon cables. Preferably, multiple ribbon cables would be physically attached along their entire length, using a suitable adhesive such as medical grade adhesive or any other suitable connection mechanism. The cable is preferably connected to the electrical subsystems through rivet bonds, ball bonds, or NEUR-P06 any other suitable connection mechanisms. The connector 34 may alternatively be seamlessly manufactured with the first and or second electrical subsystem. The connector 34 may further include fluidic channels adapted to deliver therapeutic drugs, drugs to inhibit biologic response to the implant, or any other suitable fluid.

6. The Stylet and the Guide Tube

Additionally, the system 10 may further include a stylet. The stylet of the preferred embodiments functions to penetrate the tissue or other material and/or functions to provide structural support to the system during implantation. The stylet is preferably inserted into a lumen of a carrier 16, but may alternatively be located and inserted into any suitable component of the system in any suitable manner. The stylet may include a sharpened end adapted to penetrate the tissue and aid in the insertion of the stylet, the carrier 16 and/or the electrode array 12 into the tissue. The stylet is preferably removed from the tissue following the placement of the electrode array 12, but may alternatively be adapted to remain in the tissue while still allowing the implanted electrode array 12 to float freely in the brain. This may be accomplished by the stylet being selectively flexible (through electrical stimulus or other suitable method) or by being resorbable into the tissue after a period of time. The stylet is preferably made from a stiff material such as metal, but may alternatively be made from any suitable material. In one variation, the metal is preferably insulated metal wire. In this variation, the insulated metal wire may not have insulation covering a sharpened tip, and thus can be used as a conventional single-channel microelectrode.

Additionally, the system 10 may further include a guide tube. The guide tube of the preferred embodiments functions to facilitate the insertion of the electrode array 12 and/or functions to provide structural support to the system during implantation. The guide tube may be further adapted to allow the electrode array 12 to move freely in the tissue, allowing the placement of the electrode array 12 without disconnecting the second electrical subsystem. The guide tube is preferably made of a rigid material, which can be inserted into tissue or other substances without buckling and can maintain a generally straight trajectory through the tissue. The material may be uniformly rigid, or rigid only in a particular direction (such as the axial direction). The material is preferably plastic such as a medical grade plastic, but may alternatively be any suitable material such as metal or a combination of materials. The guide tube may further include a sharpened end adapted to penetrate the tissue and aid in the insertion of the guide tube into the tissue. The guide tube may also include alignment and or fixation features to facilitate positioning and stabilizing the series of electrode array 12 in the tissue, particularly during removal of the guide tube.

7. Other Aspects of the Invention

As shown in FIG. 1A, the neural interface system 10 of the preferred embodiments includes an electrode array 12 having a plurality of electrode sites 14 and a carrier 16 that supports the electrode array. The electrode array 12 is coupled to the carrier 16 such that the plurality of electrode sites 14 are arranged both circumferentially around the carrier 16 and axially along the carrier 16. In one preferred embodiment, the electrode array 12 preferably includes both recording electrode sites 32 and stimulation electrode sites 30, as shown in FIG. 1A. In this preferred embodiment, the electrode array 12 further includes interconnects 48 ascending from the electrode array 12, as shown in FIG. 1B. The interconnects 48 transition from the outer surface of the carrier 16 into the core such that the connection point and the entire connector 34 are imbedded in silicone, as shown in FIG. 1B. To facilitate adhesion between the silicone and polymer, small nonhomogeneous perforations are preferably micromachined in the polymer substrate to allow for liquid silicone to flow into and form a robust anchor after being cured. The electrode array 12 is preferably connected to the connector 34 via the interconnects 48, as shown as FIG. 1B.

The electrode array 12 and carrier 16 are preferably assembled by a method, as shown in FIG. 7, including any of the following steps, any suitable additional steps, and any combination of steps thereof.

Connecting electrode array 12 to the connector 34. This is preferably completed with ball bonds 52, as shown in FIGS. 8A and 8B, but may alternatively include any other suitable technique. "Rivet" bonds bonding technique involves ball bonding through a hole in the polymer cable that is surrounded by an annular bond pad, to a bond pad on the device underneath. This effectively forms a rivet that connects the two devices both electrically and mechanically, as shown in FIGS. 8A and 8B.

Connecting a second electrical subsystem such as a flexible printed circuit board (PCB) to the connector 34. This is preferably completed with wire-bonds bonded to bond pads on the connector 34, but may alternatively include any other suitable technique.

Pre-forming the electrode array 12. The planar electrode array 12 will be preferably pre-formed into a 3-dimensional cylindrical form, or any other suitable form to be compatible with the carrier 16. This step is preferably completed by positioning the planar electrode array 12 in a mold and then placing the mold and electrode array 12 in a furnace to be tempered, but may alternatively be completed by any suitable process that alters the physical shape of the planar substrate.

Connecting the interconnects 48. In some variations, there may be two interconnects 48 such as ribbon cables ascending from the electrode array 12, as shown in FIG. 1B. These two interconnects 48 are preferably connected along their entire length, to form a connector 34, using a medical grade adhesive, or any other suitable connection mechanism.

Injection molding the silicone element 50, as shown in FIG. 7. This is preferably completed by providing an injection mold tool that provides for the placement of the connector 34 and connections within it, as shown in FIG. 7, and then liquid medical grade silicone will be preferably injected into the mold and thermally cured. The carrier 16 may be the distal portion of the silicone element 50, as shown in FIG. 7, wherein the electrode array 12 is wrapped around the carrier 16. Additionally, a tube may be embedded in the silicone and will act as a stylet passage 54. The tube is preferably made of a polymer such as PTFE or any other suitable material with a low coefficient of friction.

A method of implanting a neural interface system 10, as shown in FIGS. 10A-10C, preferably comprises any combination of the following steps (or any other suitable steps):
attaching the chamber 26 to the scull (preferably in a cranial burr-hole) of a patient;
implanting, through the guide tube and/or with a stylet, an electrode array 12 coupled via a connector 34 to a second electrical subsystem;
removing the guide tube over the second electrical subsystem and/or removing the stylet;
placing the second electrical subsystem within the chamber 26; and
sealing the electrical subsystems within the chamber 26.

Although omitted for conciseness, the preferred embodiments include every combination and permutation of the various electrode arrays, the various carriers, the various electrical subsystems and connectors, and the various guide tubes and stylets.

As a person skilled in the art will recognize from the previous detailed description and from the figures and claims, modifications and changes can be made to the preferred embodiments of the invention without departing from the scope of this invention defined in the following claims.

We claim:

1. A method of assembling a neural interface system comprising the steps of:
providing a planar electrode array having a plurality of electrode sites that electrically communicate with their surroundings;
providing an electrical connector;
pre-forming the planar electrode array into a 3-dimensional cylindrical form;
connecting the electrode array to the electrical connector; and
injection molding silicone about the electrical connector to form a silicone element having an end portion;
wherein the silicone element encases electrical the connector and the end portion of the silicone element is coupled to the electrode array.

2. The method of claim 1 wherein the step of pre-forming the planar array into the 3-dimensional cylindrical form is accomplished by the steps of positioning the planar electrode array in a mold and tempering the mold and the electrode array.

3. The method of claim 1, wherein the electrode sites are sized for performing deep brain stimulation.

4. The method of claim 1, wherein the electrical connector comprises one or more ribbon cables.

5. The method of claim 1, wherein injection molding the silicone element further comprises:
injection molding the silicone element with an embedded tube configured to operate as a stylet passage.

* * * * *